United States Patent [19]

Spongr et al.

[11] 4,423,328

[45] Dec. 27, 1983

[54] MEASURING SYSTEM FOR USE IN THE RADIATION MEASUREMENT OF LAYER THICKNESSES AND THE LIKE

[75] Inventors: Jerry J. Spongr, Tonawanda; John E. Tiebor, Williamsville; Boris B. Joffe, Buffalo, all of N.Y.

[73] Assignee: Twin City International Inc., Amherst, N.Y.

[21] Appl. No.: 405,442

[22] Filed: Aug. 5, 1982

Related U.S. Application Data

[63] Continuation of Ser. No. 203,873, Nov. 4, 1983, abandoned.

[51] Int. Cl.³ .............................................. G01N 23/00
[52] U.S. Cl. ................................ 250/358.1; 250/496.1
[58] Field of Search ............ 250/308, 496, 497, 358.1, 250/505

[56] References Cited

U.S. PATENT DOCUMENTS

| | | | |
|---|---|---|---|
| 2,938,124 | 5/1960 | Boyd | 250/308 |
| 3,115,577 | 12/1963 | Joffe et al. | 250/308 |
| 3,529,158 | 9/1970 | Joffe et al. | 250/496 |
| 3,588,507 | 6/1971 | Weinstock et al. | 250/308 |
| 3,705,305 | 12/1972 | Fischer | 250/358.1 |
| 3,720,833 | 3/1973 | Aag | 250/497.1 |

*Primary Examiner*—Bruce C. Anderson
*Attorney, Agent, or Firm*—Christel, Bean & Linihan

[57] ABSTRACT

A system for the radiation backscatter measurement of coating thicknesses has a stand for supporting a workpiece, and a probe body removably mounted on the stand and carrying a radiation source, a radiation detector and a sighting device, the probe body being vertically adjustable on the stand to selectively vary the height of the workpiece-receiving throat. The probe body is self-supporting independently of the stand on a workpiece or other supporting surface and can be inverted to provide its own workpiece support, being self-supporting when inverted. The source and detector are movable simultaneously as a unit with the sighting device to position first one and then the other in operative alinement with the axis of measurement.

16 Claims, 9 Drawing Figures

MEASURING SYSTEM FOR USE IN THE RADIATION MEASUREMENT OF LAYER THICKNESSES AND THE LIKE

This application is a continuation of application Ser. No. 203,873, filed Nov. 4, 1980 abandoned.

BACKGROUND OF THE INVENTION

The present invention relates generally to the measuring art, and more specifically to a new and useful system for measuring coating thicknesses utilizing beta backscatter radiation techniques.

The beta backscatter radiation technique for measuring ultra thin coating thicknesses is well known, being disclosed in U.S. Pat. No. 3,132,248 among others, and various types of apparatus have been developed for use in conjunction therewith. U.S. Pat. No. 3,115,577, for example discloses a measuring table having interchangeable apertured platens for supporting a workpiece to be measured in operative alinement with a radiation source and detector, together with an illuminating arrangement to facilitate positioning of the workpiece. U.S. Pat. No. 3,705,305 shows another table arrangement for supporting a workpiece to be measured, the table carrying a measuring head including a source and a detector, and a sighting device to align the workpiece for measurement. The measuring head is rotatable on the table for supporting the workpiece on the head itself.

For many purposes it is undesireable, if not impractical or impossible to bring the workpiece to be measured to such a table, and portable probes have been developed which can be positioned either directly on the workpiece under test or on a surface on which such workpiece is placed. U.S. Pat. No. 3,720,833, for example, shows a housing adapted to be placed, for example, directly on a circuit board, the housing containing a locator and a probe including both a radiation source and a radiation detector. When the locator has been used to position the coating under test relative to the housing, it is retracted and the probe is simultaneously lowered into position against the coating area under test, to make the measurement.

Another portable probe is shown in U.S. Pat. No. 3,529,158 wherein a guide receptacle is adapted to be positioned relative to the coating area under test, the guide then being removed from the receptacle, and replaced by a portable probe which also can be installed on a table to receive and support a coated object under test.

SUMMARY OF THE INVENTION

The primary object of this invention is to provide an apparatus for the beta backscatter measurement of coating thicknesses which is usable either in conjunction with a stand on the base of which the workpiece is supported, or independently thereof in the manner of a portable probe, which also can function as a self-contained measuring table to support the coated article under test.

Another object of this invention is to provide the foregoing in an arrangement wherein the probe body, when mounted on the stand, is vertically adjustable to selectively vary the throat opening and thereby accommodate workpieces of different sizes and configurations.

Another object of this invention is to provide the foregoing in apparatus which is capable of extreme accuracy in all modes of use, and which is extremely durable and dependable in operation.

In one aspect thereof, a measuring system of this invention is characterized by the provision of a stand adapted to support a workpiece to be measured, a probe body having a radiation source and a radiation detector, the probe body being operable for the measurement of a workpiece both in a first and in a second position of orientation of the probe body, the probe body being removably supported on the stand in its first position of orientation for measuring a workpiece supported on this stand, and being self-supporting in its first position of orientation independently of the stand, upon removal from the stand and placement directly on a workpiece or another supporting surface, the probe body also being self-supporting independently of the stand in its second position of orientation, and being adapted to support the workpiece to be measured when in its second position of orientation.

The foregoing and other objects, advantages and characterizing features of this invention will become apparent from the ensuing detailed description of an illustrative embodiment thereof, reference being made to the accompanying drawings.

DETAILED DESCRIPTION OF THE ILLUSTRATED EMBODIMENT

Figure 1:
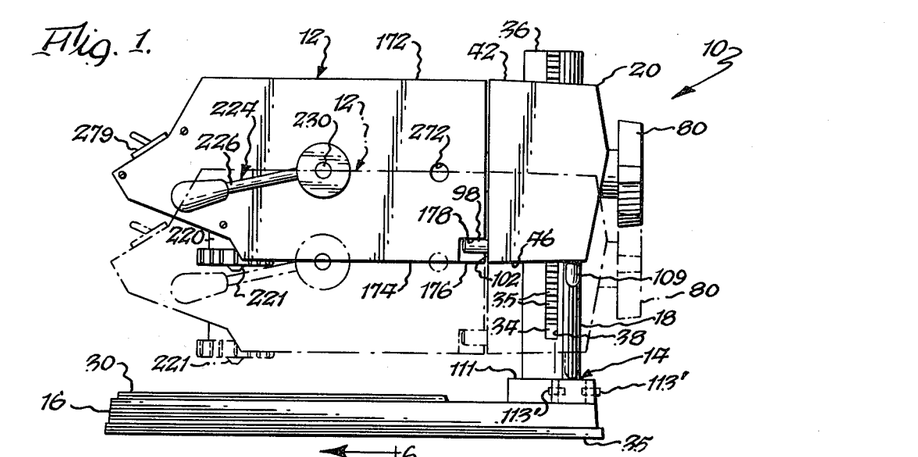
FIG. 1 is a side elevational view of a measuring system of this invention, the probe body being shown in its up position, its down position being indicated in phantom.
Figure 2:
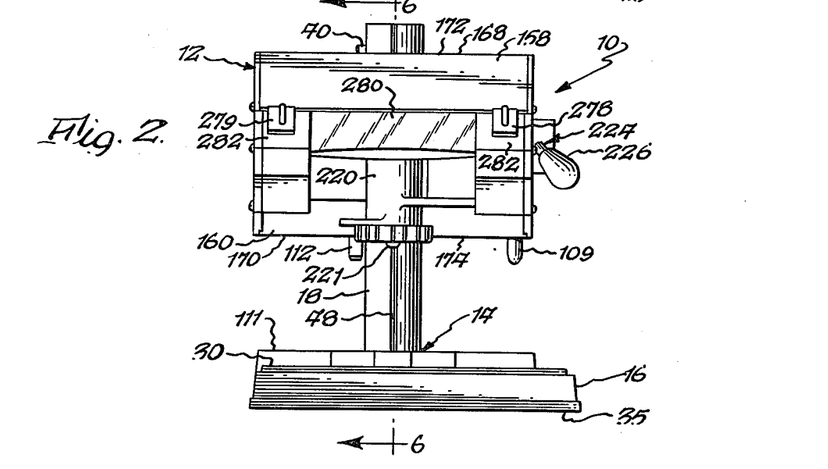
FIG. 2 is a front end elevational view thereof.

Referring now in detail to the illustrative embodiment depicted in the drawings, there is shown in FIGS. 1 and 2 a measuring system or apparatus generally designated 10 for use in conjunction with beta radiation measurements to determine coating thickness. Apparatus 10 generally includes a probe body 12 and a stand 14 comprising a horizontal base 16, an upstanding base shaft 18 and a mounting support 20 for the probe body, the support 20 being vertically adjustable on shaft 18.

Figure 6:
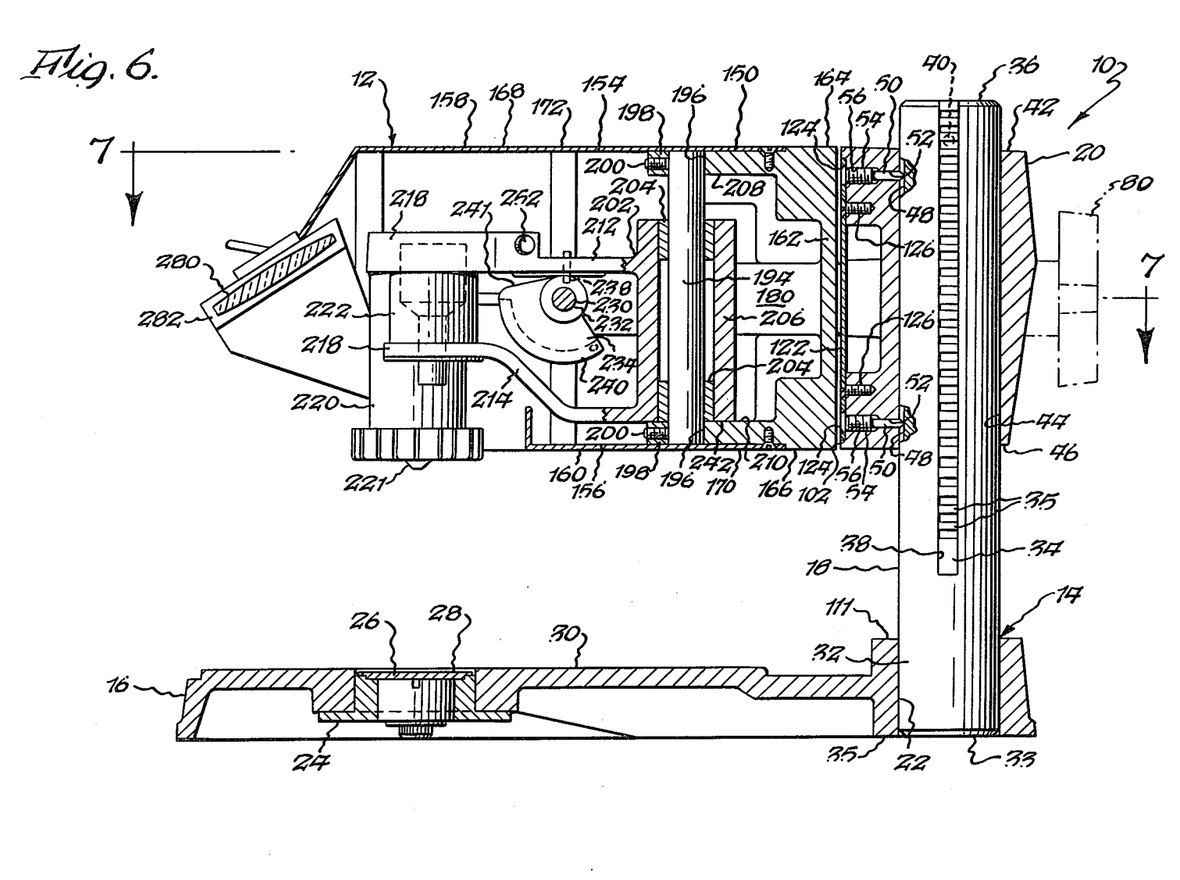
FIG. 6 is a vertical sectional view of the probe body in position on the stand, taken about on line 6—6 of FIG. 2.

Base 16 is a casting having a generally rectangular configuration in plan view. As shown in FIG. 6, base 16 has an opening formed through a generally central portion adjacent the front end thereof for receiving a platen support 24. Support 24 is shouldered to mount a disc 26 with its top surface 28 parallel and approximately in the same plane as surface 30 of base 16. Disc 26 is intended to support a workpiece to be measured, as described hereinafter.

Base 16 also has a vertically extending cylindrical socket 22 formed through a generally central portion of the rearward end thereof. The lower end 32 of shaft 18 is press fitted or otherwise snugly inserted into socket 22, such that flat end face 33 of shaft 18 is flush with the bottom surface 35 of base 16, and shaft 18 extends vertically upward from base 16 perpendicular to the upper surface 30 thereof. Shaft 18 is provided with a narrow rack 34 having vertically aligned teeth 35 extending normal to upper base surface 30. Rack 34 is fixed in a groove 38 extending from the upper end 36 of shaft 18 downwardly along one side of the shaft a suitable distance to permit support 20, and with it probe body 12, to be selectively adjusted to a wide variety of vertically spaced operable positions with respect to disc 26. In the preferred embodiment, rack 34 is formed from nylon and inserted in groove 38 such that no portion of rack 34 extends laterally outward beyond the circumferential periphery of base shaft 18. A stop pin 40 (FIG. 2) projects outwardly beyond the circumferential periphery of shaft 18 diametrically opposed to rack 34 and a selected distance from the top 36 to limit vertical movement of probe body support 20 upon contact with the upper surface 42 thereof.

Figures 7, 8:
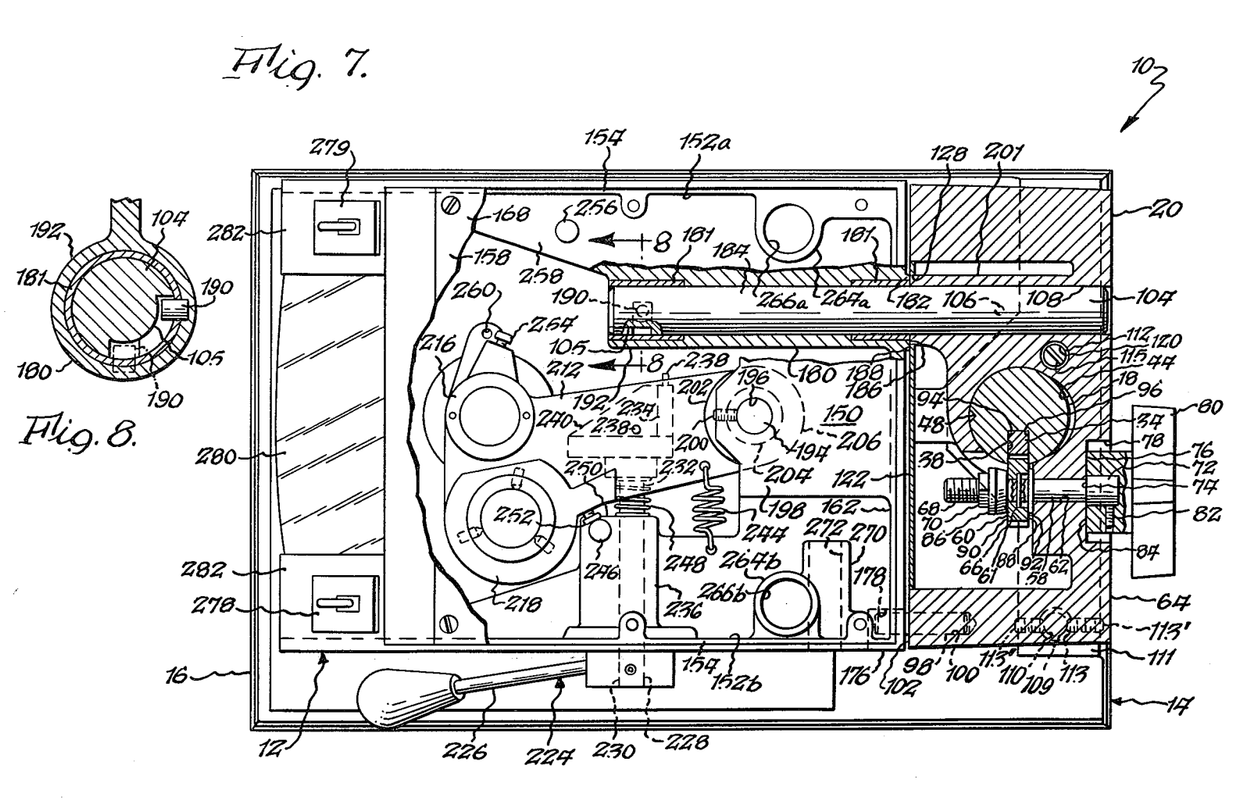
FIG. 7 is a view, partly in horizontal section and partly in plan, taken about on line 7—7 of FIG. 6.
FIG. 8 is a fragmentary sectional view taken about on line 8—8 of FIG. 7.

Probe body support 20 has a vertical opening 44 formed generally centrally therethrough from upper surface 42 to lower surface 46 through which base shaft 18 extends, as shown in FIG. 6. A shallow groove 48 is formed in shaft 18 approximately midway between rack 34 and stop pin 40 and extending the entire length of shaft 18 to receive a pair of lock pins 50 extending through cylindrical bores 52 in support 20 in spaced relation to one another in a common vertical plane and having parallel longitudinal axes. Set screws 54 countersunk in counterbores 56 hold lock pins 50 in engagement against shaft 18 in groove 48 and are suitably adjusted to maintain a selected degree of friction or drag between lock pins 50 and shaft 18 to minimize vertical and rotational slippage of probe body support 20 relative to shaft 18, to foster precise vertical movement of support 20, and to assist in maintaining the adjusted position of support 20. As shown in FIG. 7, a stepped shaft 58 having a spur gear 60 concentrically mounted thereon is journaled in a cylindrical bore 62 in the rear wall 64 of support 20, generally perpendicular to and adjacent shaft 18 such that the teeth 66 of spur gear 60 mesh with teeth 35 of rack 34. The rear wall 64 of support 20 has a knob receiving recess 78 formed therein, having a flat surface 76 adjacent bore 62 to limit the movement of knob shaft 58 inward through bore 62. The interior end 68 of knob shaft 58 is threaded to accept a nut 70 and the head 72 of knob shaft 58 is of slightly larger outer diameter than the diameter of bore 62, providing a shoulder 74 which abuts the inner wall surface 76 of recess 78. A knob 80 is concentrically mounted on head 72 by set screw 82 so that rotational motion of knob 80 is transferred to shaft 58. The end surface 84 of knob 80 is generally flush with shoulder 74 of knob shaft 58 and also abuts the flat surface 76 of knob receiving recess 78. Spur gear 60 is maintained in position on knob shaft 58 by nut 70 and spacer 86 which hold gear 60 against a pin 61 extending diametrically through shaft 58. The outer portion 88 of the faces 90, 92 of spur gear 60 are received between parallel side walls 94, 96 of groove 38 in shaft 18, and shoulder 74 of knob shaft 84 combines with these elements to limit the lateral movement of spur gear 60 with respect to rack 34. Upon manual rotation of knob 80, support 20 can be raised and lowered relative to base 16.

As shown in FIGS. 1 and 7, a stop 98 is press fit into a cylindrical bore 100 in a lower corner portion of the forward face 102 of support 20 and projects outwardly beyond the forward face 102 generally normal to shaft 18 and parallel to upper surface 30 of base 16. A horizontal mounting shaft 104, having a generally L-shaped bayonet slot 105 formed at the leading end thereof (FIG. 8) is fixed in a cylindrical bore 108 running horizontally through support 20 from rear face 64 to forward face 102 by a set screw 106. Shaft 104 projects outwardly from forward face 102 considerably beyond stop 98, axially parallel to but horizontally and vertically spaced therefrom to receive and mount probe body 12.

A fixed locating pin 109 is press fit into a cylindrical bore 110 in the lower surface 46 of housing support 20 and projects outwardly therefrom in spaced relation and perpendicular to stop 98. A corresponding cylindrical bore 113 is formed through raised surface 111 of base 16, as shown in FIG. 1, in axial alignment with locating pin 109 to receive the same when support 20 is lowered on shaft 18. Bore 113 is of greater diameter than pin 109. To provide positive locating of support 20 and probe body 12 when mounted thereon, a pair of adjustable locating screws 113' are carried by surface 111 in opposed relation, the screws 113' entering bore 113 to receive pin 109 with only working clearance therebetween. The position of pins 113' can be adjusted to accommodate variations due to manufacturing tolerances.

For ease of repeatability in lowering support 20 and probe body 12 to a preselected position relative to disc 26, an adjustable stop 112 is threaded in a vertical cylindrical bore 120 through support 20 from the upper surface 42 to the lower surface 46 parallel to and adjacent shaft 18 and on the opposite side of shaft 18 from fixed pin 109. Stop 112 projects downwardly a selected distance below the lower surface 46 to engage base surface 111, and has a slotted upper end, indicated at 115 in FIG. 7, to receive a tool for selectively adjusting the vertical position of the stop. A cover plate 122 (FIG. 6) having a pair of apertures 124 formed therein through which set screws 54 may be inserted, withdrawn and adjusted, and an opening 128 through which horizontal mounting shaft 104 projects, is attached to support 20 by means of screws 126 so as to be flush with forward face 102 for the protection of the knob shaft, spur gear and rack assembly previously described.

As shown in FIGS. 6 and 7, probe body 12 comprises a unitary, generally U-shaped body member 150 of cast aluminum, for example, having parallel, spaced side walls 152a, 152b with parallel top and bottom edges 154, 156 respectively, a back wall 162 perpendicular to and connecting side walls 152a, 152b at one end thereof. Flat, parallel, top and bottom cover plates 158, 160 respectively, extend between and are removably attached to side walls 152a, 152b at the top and bottom edges 154, 156 thereof by means of screws or other suitable fasteners. Back wall 162 is shouldered to receive cover plates 158, 160, whereby the outer surfaces 168, 170 thereof respectively provide a substantially flush continuation of top and bottom surfaces 164, 166 respectively to form planar, parallel top surface 172 and bottom surface 174 of body 12. As shown in FIG. 1, back wall 162 of probe body 12 has a notched corner 176 formed to receive and engage stop 98 and has a contact surface 176 which rests on top of stop 98 when body 12 is attached to support 20 to maintain body 12 in a horizontal plane parallel to the plane of disc 26, and to prevent clockwise rotation of body 12 about shaft 104 beyond this position.

As shown in FIG. 7, probe body 12 has a horizontally disposed cylindrical sleeve portion 180 integrally formed therewith and providing a bore therethrough adapted to receive a bronze bushing 181 in a counterbore at each end of the sleeve 180. The bore of sleeve 180 extends longitudinally through body member 150. Back wall 162 has an outwardly protruding collar portion 182 which surrounds the rearward end of the sleeve bore. Sleeve 180 is located in body 12 such that when the exposed end 184 of mounting shaft 104 is completely inserted into sleeve 180, the end surface 186 of collar 182 is flush with and abuts against the body of support 20, which protrudes through face 188 of cover plate 122, and upon rotation against stop 98 probe body 12 is generally in horizontal and vertical alinement with support 20. Sleeve 180 is substantially coextensive in length with the projecting end 184 of mounting shaft 104, and shaft 104 is journaled in bushings 181 when inserted into sleeve 180. As shown in FIGS. 7 and 8, a guide pin 190 mounted in the inner end 192 of sleeve 180 projects radially inward through an opening provided in the innermost bushing 181 toward the longitudinal axis of sleeve 180 a distance slightly less than the depth of slot 105 for working clearance therein, as described hereinafter.

As shown in FIGS. 6 and 7, a vertical shaft 194 is located between side walls 152a, 152b, being disposed perpendicularly between covers 158, 160 in apertures 196 formed in flanges 198 of body member 150 and held in stationary position by a pair of set screws 200 contacting opposite ends thereof. An armature 202 is slideably and rotatably journaled on shaft 194 by means of bushings 204 inserted within a hollow cylindrical hub portion 206 of armature 202. Horizontal surfaces 208, 210 of flanges 198 serve as upper and lower stops, respectively, to limit the vertical movement of armature 202 by engagement with the opposite ends of hub 202. Surface 210 also acts as a supporting surface for armature 202 in its downwardmost position as shown in FIG. 6. Instrument holder arms 212, 214 are integrally formed with hub 206 and extend radially outwardly from hub 206 at an acute angle relative to each other. At the outermost extension of arms 212, 214 holding collars 216, 218 formed integrally therewith, are adapted to hold a measuring head or probe 220 and a sighting device 222 respectively in vertical orientation with their axes parallel to each other and perpendicular to surface 28 of disc 26. The longitudinal axes of probe 220 and sighting device 222 lie radially equidistant from the longitudinal axis of shaft 194, whereby armature 202 can be rotated about shaft 194 to selectively place either probe 220 or sighting device 222 in alignment with the workpiece to be measured.

Figure 4:
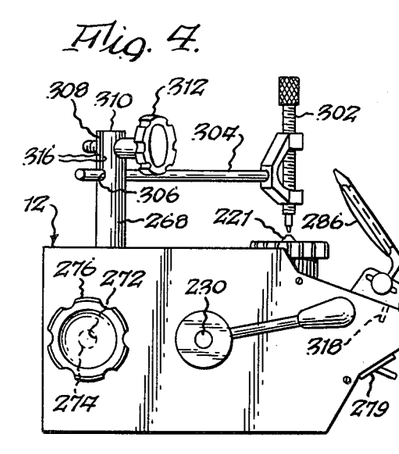
FIG. 4 is a side elevational view showing the probe body inverted and functioning as a measuring table.
Figure 5:
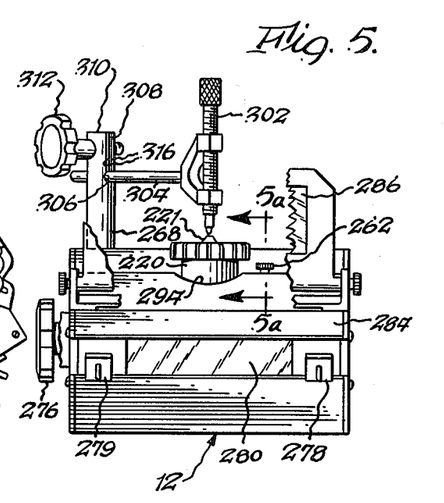
FIG. 5 is a front end elevational view of the probe body of FIG. 4, the lens being broken away for clarity.

In this manner, sighting device 222 can be rotated into operating position to line up a workpiece on disc 26 for measurement, and can then be rotated out of operating position while probe 220 is simultaneously rotated into the identical operating position previously occupied by sighting device 222 for taking a measurement. As a result, sighting device 222 and measuring head 220 are never in axial alignment with one another. Sighting device 222 is at all times located within the confines of body 12, i.e. it does not extend outward beyond cover plates 158, 160 or side walls 152a, 152b of the probe body housing. This permits probe body 12 to be inverted and used as a measuring table as shown in FIGS. 4 and 5. Measuring head 220, on the other hand, is confined between side walls 152a, 152b but may extend below bottom cover plate 160. Measuring head 220 includes a GM tube, apertured platen 221 and isotope source, and sighting device 222 projects illuminated crosshairs, all in a manner well known in the beta radiation measurement art, and further discussion of their construction and operation therefore is unnecessary. Rotational movement of armature 202 about shaft 194, and vertical movement of armature 202 along shaft 194, are accomplished by manipulating a linkage generally designated 224 comprising a handle 226 connected to one end 228 of a shaft 230 on the other end 232 of which is mounted a cam 234. Shaft 230 is journaled horizontally in side wall 152b of body 12 and rotates in a cylindrical boss 236 projecting inward from side wall 152b as shown in FIG. 7. A cam follower in the form of pin 238 projecting through arm 212 rides on the throw surface 240 of cam 234. The follower could be a roller. When handle 226 is in the forward position as shown in FIG. 7, measuring head 220 is in its lowermost position as shown in FIG. 6 wherein one end 242 of armature hub 206 has bottomed on flange surface 210 and probe 220 is in measuring alignment with the center disc 26. In this position, spring 244 biases armature 202 against a first stop post 246, to maintain probe 220 in operative alignment.

As handle 226 is thrown clockwise through an arc of approximately 180° from its forward position shown in the drawings to a rearward position, (not shown), arm 212 is initially picked up by surface 24 of cam 234, causing armature 202 to lift a predetermined distance from flange surface 210. Then, follower 238 is engaged by throw surface 240, causing measuring head 220 to rotate or swing out of position while simultaneously swinging sighting device 222 into operating position for lining up a workpiece for measurement. A spring 248 is mounted over shaft 230 between cam 234 and the end face 250 of boss 236 and biases cam 234 away from end face 250 and toward cam follower 238, to maintain their engagement. Spring 244 holds armature 202 against rotational movement about shaft 194 when measuring head 220 is in measuring position and handle 226 is in forward position. An adjustable first stop screw 252 mounted horizontally on arm 214 contacts first stop post 246 extending vertically outward from cylindrical boss 236 as shown in FIG. 7 to prevent spring 244 from pulling armature 202 in a counterclockwise direction about shaft 194 beyond the preselected measuring position of measuring head 220. An adjustable second stop screw 254 is mounted on arm 212 to contact a second stop post 256 projecting vertically outward from flange surface 258 of body member 150 to prevent clockwise rotation of armature 202 about shaft 194 beyond the preselected operating position of sighting device 222, such that sighting device 222 is in operating position when stop screw 254 is in contact with stop post 256. When handle 226 is in the forward position, as shown in FIG. 7, stop screw 252 is in contact with stop post 246 and measuring head 220 is in operative position. When handle 226 is in its rearward position (not shown), stop screw 254 is in contact with stop post 256 and sighting device 222 is in operative position. As handle 226 travels to the rearward position, pin 238 rides on cam surface 240 forcing armature 202 toward stop 256 and extending spring 244 to its greatest required extension. As handle 236 is returned into the forward position, pin 238 retraces its route travelled on cam surface 240 as the handle traveled to its rearward position, causing armature 202 to rotate toward stop post 246 and causing spring 244 to retract and hold stop screw 252 against stop post 246.

Figure 5A:
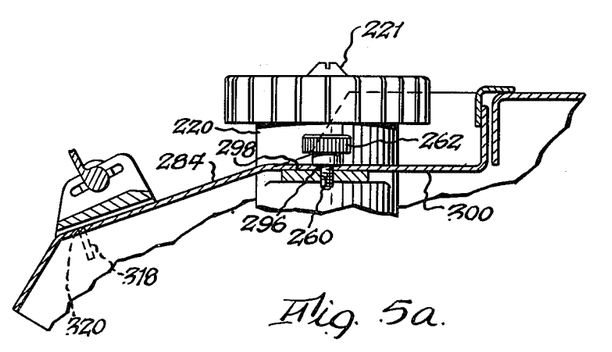
FIG. 5a is a fragmentary, sectional view, on an enlarged scale, taken about on line 5a—5a of FIG. 5.

Arm 212 has an aperture 260 formed therein for receiving a thumbscrew 262 as shown in FIG. 5a for maintaining measuring head 220 in a fixed position when it is to be used as a support surface as well as a measuring device as shown in FIGS. 4, 5, and 5a.

As shown in FIG. 7, a pair of opposing vertical bosses 264a, 264b integrally formed with opposed side walls 152a, 152b respectively have cylindrical bores 266a, 266b formed therein for accepting a vertical mounting post 268 as shown in FIGS. 4 and 5 in either one of such bores so that it projects vertically outward through one of a pair of corresponding apertures (not shown) formed in cover plate 158. A pair of opposing horizontal bosses 270 (only one shown in FIG. 7) having cylindrical bores 272 formed therein project generally horizontally and inwardly through side walls 152a, 152b, adjacent bosses 264a, 264b for accepting an arcuately notched, cylindrical puller 274 having a thumb wheel 276 engaging a threaded end thereof as shown in FIGS. 4 and 5. The notched portion of puller 274 is formed to fit over a portion of the circumferential periphery of mounting post 268. As shown in FIG. 7, a portion of bores 272 and bores 264a, 264b intersect so that when puller 274 is inserted into bore 272, post 268 can then be mounted in the corresponding bore 266a, 266b only when the notched portion of puller 274 is positioned to fit around the portion of the circumferential periphery of post 268 that intersects bore 272. When post 268 is thus mounted, thumb wheel 276 is turned in the appropriate direction to draw puller 274 outwardly forcing an inward edge of the notched portion against a corresponding peripheral portion of post 268 wedging and thereby releasably securing the post in position.

The forward ends of side walls 152a, 152b of housing 12 have inclined surfaces supporting a pair of laterally spaced control switches 278, 279 and a generally rectangular magnifying lens 280 held in place by a pair of retainers 282 located between side walls 152a, 152b. Switches 278, 279 are mounted on retainers 282.

Figure 3:
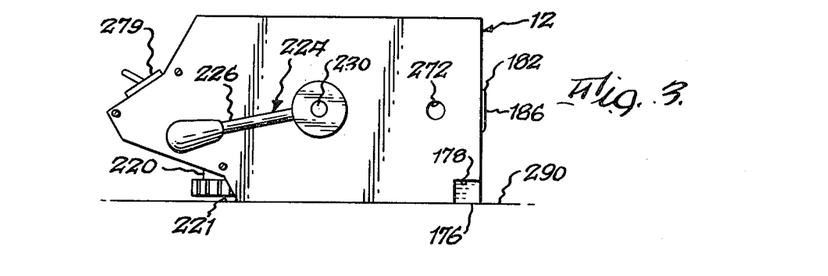
FIG. 3 is a side elevational view of the probe body removed from its stand and shown in operative position on a work surface.

When measuring head 220 is used as a support surface as shown in FIGS. 4, 5 and 5a, side walls 152a, 152b support an auxiliary cover 284 therebetween adapted to be positioned on the lower portion of the forward end of housing 12 as viewed in FIGS. 1–3. Cover 284 also is adapted to receive a magnifying lens assembly 286 inserted therein and positioned for viewing a workpiece held between measuring head 220 and a holder stem 302 shown in FIGS. 4 and 5.

In a first or stationary operative mode as shown in FIGS. 1, 2, 6 and 7, the probe body 12 is mounted on the stand 14, being suspended horizontally over and generally parallel to base 16 by support 20. The probe body 12 can be raised and lowered by turning knob 80 in the appropriate direction. With probe body 12 raised, the workpiece is placed on disc 26. Handle 226 is then swung vertically through a clockwise arc of approximately 180° to its rearward position, bringing sighting device 222 into alignment with the workpiece and swinging measuring head 220 out of the way. The workpiece is aligned for accurate measurement by the sighting device 222 projecting a cross hair onto the workpiece, the body 12 being raised or lowered to achieve a sharp focus. The magnifying lens 280 enables the operator of the measuring device to more easily and accurately align the workpiece with the sighting device 222 prior to measurement. Once the workpiece has been aligned, handle 226 is swung through a counterclockwise arc returning handle 226 to its forward position and thereby moving measuring head 220 into measuring position while simultaneously rotating sighting device 222 out of the way. In this position, measuring head 220 projects below the body to position the apertured platen 221 against the workpiece. Stop 112 can be adjusted for use when housing 12 is to be lowered repetitively to a selected distance from disc 26. This feature is particularly useful for measuring a plurality of parts having identical dimensions.

In a portable or second operative mode as depicted in FIG. 3, the probe body 12 has been removed from the stand 14 and placed on the surface 290 which can be a workpiece to be measured or a table or other surface on which the workpiece is placed. To remove probe body 12 from stand 14, support 20 is first raised above upper surface 30 of base 16 a sufficient distance to permit clearance for rotating probe body 12 90° counterclockwise about shaft 104 from the position shown in FIG. 1 without interference from surface 30. The probe body 12 is removed from the stand 14 by rotating the body 12 approximately 90° about shaft 104 in a counterclockwise direction from the horizontal position shown in FIGS. 1 and 2, then pulling body 12 forward away from support 20 until sleeve 180 has been completely withdrawn off shaft 104. Probe body 12 is then free to be placed on a surface 290 which is remote from stand 14 or too large to be accommodated on stand 14, as shown in FIG. 3. It is apparent that measuring head 220 and sighting device 222 will be held with their axes normal to the surface 290 when the bottom surface 174 of housing 12 abuts against the planar surface 290. If the measuring head 220 is in operating position when the housing 12 is lowered to surface 290, probe 220 automatically lifts so as to avoid inadvertant damage because armature 202 is free to slide upward along shaft 194 when probe 220 contacts the surface 290. The sighting device 222 and the measuring head 220 may then be rotated into and out of position, as described above in the discussion of the first operative mode, to line up and measure the workpiece. It should be noted that this ability to use the same method for aligning the workpiece for measurement as is utilized in the stationary mode overcomes the need for using a unique, separate locating guide in conjunction with the measuring device or providing locating guide lines on the device itself to accurately line up the workpiece.

In a third operative mode shown in FIGS. 4, 5 and 5a, the probe body 12 has been removed from the stand 14 and is inverted so that what is normally the top surface of probe body 12 now becomes the bottom surface and rests upon any convenient, preferably flat, horizontal support surface. Since armature 202 is free to slide upward on shaft 194 as described above, the force of gravity will draw armature 202 toward surface 208 in this inverted position. In order to maintain platen 221 of measuring head 220 projecting outwardly beyond the surface of probe body 12, auxiliary cover 284 is provided with a first opening 294 through which measuring head 220 projects outwardly beyond cover 284 and a second opening 296 located to correspond to the location of threaded aperture 260 in arm 212. When surface 298 of arm 212 approaches surface 300 of auxiliary cover 284, thumb screw 262 may be inserted through second opening 296 into aperture 260 to draw armature 202 toward cover 284 and hold armature 202 in abutting relation to cover 284, and thus retain measuring head 220 at a selected fixed level. In this mode, handle 226 is maintained in the forward position described above throughout operation. A workpiece to be measured is placed on the end surface of platen 221 and is maintained in position thereon by a vertically adjustable holder stem 302 carried at one end of a horizontal holder arm 304 which is slip fit through a circular opening 306 through vertical mounting stem 268, and suspended horizontally therefrom. A longitudinal slot 308 extends from the top end 310 of mounting stem 268 and intersects circular opening 306. The horizontal distance which holder arm 304 projects from mounting stem 268 is adjustably maintained by tightening a thumb screw 312 projecting through an opening (not shown) located near the top end 310 of mounting stem 268 through a diameter thereof that is oriented at a right angle with respect to circular opening 306 and generally perpendicular to slot 308 such that the surfaces 316 of slot 308 are drawn toward one another causing holder arm 304 to be securely clamped in opening 306. Mounting stem 268 can be inserted in either of the two bores 266a, 266b provided in the casting as referred to above. Puller 274 is then inserted into the corresponding bore 272 as previously described to securely hold mounting stem 268 in place.

Magnifying lens assembly 286 having a pair of pins 318 projecting therefrom, only one of which is shown, is inserted into corresponding apertures 320 provided in auxiliary cover 284 to aid the operator in lining up the holder stem 302 with a workpiece resting on platen 221. Assembly 286 also acts as a radiation shield. Once the workpiece is held securely in position, the requried measurement can be made.

Accordingly, it is seen that our invention fully accomplishes its intended objects. The probe body can be used in conjunctin with the stand, and the height of the workpiece receiving throat can be selectively adjusted. The probe body can be removed from the stand and is self supporting both in its normal position of use and when it is inverted to provide a self contained measuring table.

Having disclosed and described a specific embodiment of our invention, it will be appreciated that this has been done by way of illustration only, and that the scope of this invention is intended to be defined by the appended claims.

We claim:

1. A measuring system for use in the radiation measurement of layer thicknesses comprising a stand having means for supporting a workpiece to be measured, a probe body having a radiation source and a radiation detector, said probe body being movable for the measurement of a workpiece in both a first and a second position of orientation of said probe body, support means for removably supporting said probe body on said stand in said first position of orientation for measuring a workpiece supported on said stand and said probe body being removable said stand for use in said second position of orientation for measuring a workpiece supported by said probe body, said probe body being self-supporting in said first position of orientation independently of said stand upon removal from said stand and placement directly on a workpiece or another workpiece supporting surface, and said probe body also being self-supporting on a supporting surface upon removal from said stand and placement in said second position of orientation, said probe body including means to support a workpiece to be measured when in said second position of orientation.

2. A measuring system as set forth in claim 1, said means for removably supporting said probe body on said stand including means for selectively adjusting the spacing between said probe body and said workpiece supporting means, thereby providing a selectively variable clearance therebetween to accommodate workpieces of different dimensions.

3. A measuring system as set forth in claim 1, wherein said first and second positions of orientation normally are generally horizontal, and said probe body is inverted to provide said second position upon removal from the stand.

4. A measuring system as set forth in claim 1, wherein said radiation source and said radiation detector are combined in a probe carried by said probe body, a sighting device carried by said probe body for positioning a workpiece to be measured in proper alignment with an axis of measurement, and means for moving said probe and said sighting device simultaneously as a unit into and out of operative position relative to said axis.

5. A measuring system as set forth in claim 4, wherein said last-named means includes an armature mounted for pivotal movement about a pivot axis parallel to said axis of measurement, said probe and said sighting device being carried by said armature for movement therewith, said armature being mounted for movement along said pivot axis, and cam means for pivoting said armature between a first position placing said sighting device in operative alinement with said measuring axis and a second position placing said probe in operative alinement with said measuring axis, said cam means including means for selectively moving said armature along said pivot axis in said second position.

6. A measuring system as set forth in claim 5, said cam means including a shaft journaled in said probe body, together with a handle connected to said cam shaft for selectively pivoting said armature and moving the same along said axis.

7. In a measuring system for use in the radiation measurement of layer thicknesses and comprising a stand having means for supporting a workpiece to be measured, a probe body having a radiation source and a radiation detector carried in a probe, means for accurately positioning said probe for measuring a workpiece supported on said stand, said last-named means including means for selectively adjusting the spacing between said probe and said workpiece supporting means, thereby providing a selectively variable clearance therebetween to accommodate workpieces of different heights, the improvement comprising:
 (a) said probe body being movable for the measurement of a workpiece in both a first and a second position of orientation of said probe body and capable of being self-supporting in both said first and said second positions of orientation;
 (b) carrying means positioned within said probe body for simultaneously carrying said probe and said positioning means, said carrying means supported for movement about an axis from a first position wherein said positioning means overlies said workpiece and said probe is displaced laterally from said workpiece to a second position wherein said probe overlies said workpiece and said positioning means is displaced laterally from said workpiece; and (c) means for selectively moving said carrying means between said first and said second positions.

8. A measuring system as set forth in claim 7, said stand comprising a base and an upstanding base shaft, together with a probe body mounting support receiving said base shaft, and cooperating rack and gear means carried by said shaft and support for selectively raising and lowering said support and with it said probe body.

9. A measuring system as set forth in claim 8, together with guide means maintaining the orientation of said support as it is raised and lowered, and friction means automatically operable to maintain the adjusted position of said support along said shaft.

10. A measuring system as set forth in claim 9, wherein said guide and friction means comprise vertically spaced pins carried by one of said support and shaft frictionally engaged in a vertical groove in the other thereof.

11. A measuring system as set forth in claim 8, together with adjusable stop means for repetitively positioning said probe body a preselected distance from said base.

12. A measuring system as set forth in claim 11, wherein said adjustable stop means projects from said support for engagement with said base.

13. A measuring system as set forth in claim 8, together with locating pin means carried by said support engageable in locating bore means in said base upon lowering said support.

14. A measuring system as set forth in claim 1, wherein said means for removably supporting said probe body on said stand include a mounting shaft carried by said stand, a shaft receiving sleeve carried by said probe body, coacting guide means carried by said sleeve and said shaft for assembling said probe body on said shaft in a position of orientation other than said first position and then enabling rotation of said probe body about said mounting shaft into said first position, and stop means preventing rotation of said probe body beyond said first position.

15. A measuring system for use in the radiation measurement of layer thicknesses comprising a probe body having a radiation source and a radiation detector, said probe body being operable for the measurement of a workpiece in both a first and a second position of orientation of said probe body, said probe body being self-supporting in said first position of orientation for placement directly on a workpiece or another workpiece supporting surface, and said probe body also being self-supporting on a supporting surface in said second position of orientation, said probe body being adapted to support a workpiece to be measured when in said second position of orientation.

16. A measuring system as set forth in claim 1 or claim 15, together with a mounting post carried by said probe body in said second position of orientation, means for releasably securing said post in said probe body, and means connected to said post for holding in position for measurement a workpiece supported by said probe body.

* * * * *